United States Patent
Hagaman

(10) Patent No.: US 10,391,023 B2
(45) Date of Patent: Aug. 27, 2019

(54) COLD FOOT PAIN RELIEVER

(71) Applicant: Kipp Andrew Hagaman, West Des Moines, IA (US)

(72) Inventor: Kipp Andrew Hagaman, West Des Moines, IA (US)

( * ) Notice: Subject to any disclaimer, the term of this patent is extended or adjusted under 35 U.S.C. 154(b) by 716 days.

(21) Appl. No.: 14/991,425

(22) Filed: Jan. 8, 2016

(65) Prior Publication Data
US 2017/0196765 A1   Jul. 13, 2017

(51) Int. Cl.
*A61H 15/00* (2006.01)
*A61H 15/02* (2006.01)
*A61F 7/10* (2006.01)
*B29C 41/04* (2006.01)
*B29C 41/20* (2006.01)
*A61F 7/00* (2006.01)

(52) U.S. Cl.
CPC ............ *A61H 15/02* (2013.01); *A61F 7/103* (2013.01); *B29C 41/04* (2013.01); *B29C 41/20* (2013.01); *A61F 2007/0045* (2013.01); *A61F 2007/0047* (2013.01); *A61F 2007/108* (2013.01); *A61H 2015/0042* (2013.01); *A61H 2201/0192* (2013.01); *A61H 2201/0207* (2013.01); *A61H 2201/0214* (2013.01); *A61H 2201/0257* (2013.01); *A61H 2201/1253* (2013.01); *A61H 2201/164* (2013.01); *A61H 2201/169* (2013.01); *A61H 2201/1635* (2013.01); *A61H 2205/12* (2013.01)

(58) Field of Classification Search
CPC ............ A61H 15/02; A61H 2201/0192; A61H 2201/0207; A61H 2201/164; A61H 2201/1635; A61H 2201/1253; A61H 2201/0257; A61H 2201/169; A61H 2205/12; A61H 2201/0214; B29C 41/20; B29C 41/04; A61F 7/103
See application file for complete search history.

(56) References Cited

U.S. PATENT DOCUMENTS

| 5,697,961 | A | * | 12/1997 | Kiamil | A61F 7/02 126/204 |
| 5,868,689 | A | * | 2/1999 | Faroky | A61H 15/0092 601/120 |
| 2005/0015032 | A1 | * | 1/2005 | Stein | A61H 15/02 601/131 |
| 2011/0071446 | A1 | * | 3/2011 | Citrin | A61H 15/00 601/135 |
| 2015/0238348 | A1 | * | 8/2015 | Kamat | A61H 15/00 601/19 |

* cited by examiner

*Primary Examiner* — Quang D Thanh
(74) *Attorney, Agent, or Firm* — Brett J. Trout

(57) ABSTRACT

A system for adding pressure and extracting heat from the bottom of a user's foot to aid in pain relief. A spherical container is provided with an aqueous polymer mixture which may be cooled or heated to allow heat to be transferred through the spherical container to/from the bottom of a user's foot. The spherical container is provided with a tube passing therethrough to allow a user to provide a strap through the spherical container. The strap is provided with handles to allow the user to direct the pressure of the spherical container to the bottom of the user's foot and to extract or apply heat as desired.

17 Claims, 4 Drawing Sheets

COLD FOOT PAIN RELIEVER

TECHNICAL FIELD

The disclosed embodiments relate generally to a foot pain reliever, in particular, to a foot pain reliever for applying pain relief to, and extracting heat from, the bottom of a user's foot.

BACKGROUND OF THE INVENTION

Sufferers of foot pain resulting from plantar fasciitis or heel spurs often seek relief by rolling balls or rollers under the feet. Such devices may include a rigid ball provided with a hole in the middle and a strap passing through the hole to allow the user to roll the ball under the foot while maintaining the desired positioning of the ball against the bottom of the foot. One drawback associated with such systems is the inability to use these systems in conjunction with cold therapy to increase the pain relieving effects of the device. As such devices are typically made of wood or similar material which is insulated, they are therefore not well-suited for the transfer of heat away from the foot into the device.

It is also known in the art to provide a cold compress to the bottom of the foot to reduce pain. Such devices are similar to those described in U.S. Pat. No. 5,697,961 which is incorporated herein by reference. In such devices, discreet particles of a crosslinked water-absorbing polymer polyacrylamide or sodium polyacrylate are provided within a flexible container which may then either heated or cooled before applying the device to the bottom of a foot. One drawback associated with such prior art devices is that such devices lack the rolling component known to further reduce pain across the bottom of a user's foot. It would therefore be desirable to provide a rolling device which may be directed to a particular portion of a user's foot and which may be heated or cooled to provide further pain relief. The difficulties encountered hereinabove are substantially limited by the present invention.

SUMMARY OF THE DISCLOSED SUBJECT MATTER

The deficiencies described above are overcome by the disclosed implementation of a cold foot pain reliever. The foot pain reliever acts as heat removal device to remove heat from the foot of a user. The device has a spherical container having a thermally conductive surface defining an interior. A channel is provided through the container to allow for the attachment of a strap. Provided within the hollow interior of the spherical container is a mixture of a crosslinked water-absorbing polymer mixed with water. A user cools the device and then rolls the device under the foot of the user, using handles on the strap for guidance. Other implementations of a cold foot pain reliever are disclosed, including implementations directed to systems having alternative internal and exterior components.

BRIEF DESCRIPTION OF THE DRAWINGS

The present invention will now be described, by way of example, with reference to the accompanying drawings in which.

DETAILED DESCRIPTION OF THE DRAWINGS

The system of the present invention allows a user to apply pressure to the underside of the foot while removing heat therefrom. The system described below is distinguished over earlier systems in that the present system provides a heat removal feature.

Figure 1:
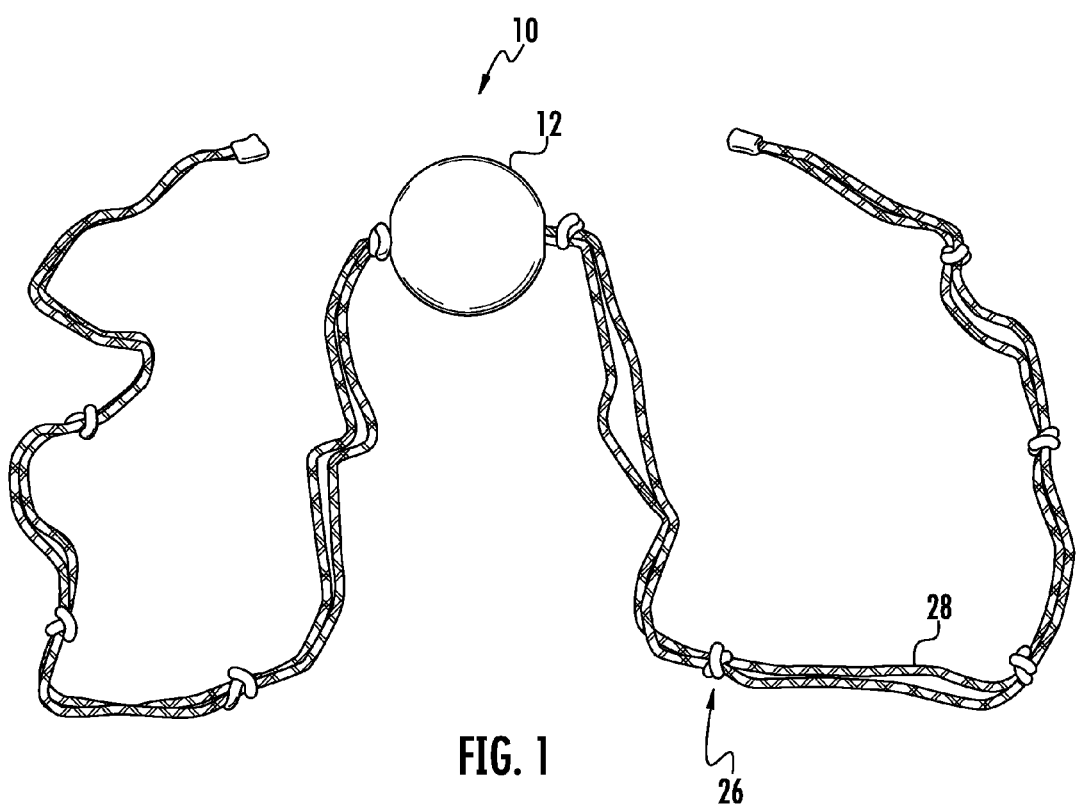
FIG. 1 illustrates a top perspective view of the pain relief device in accordance with one embodiment.
Figure 4:
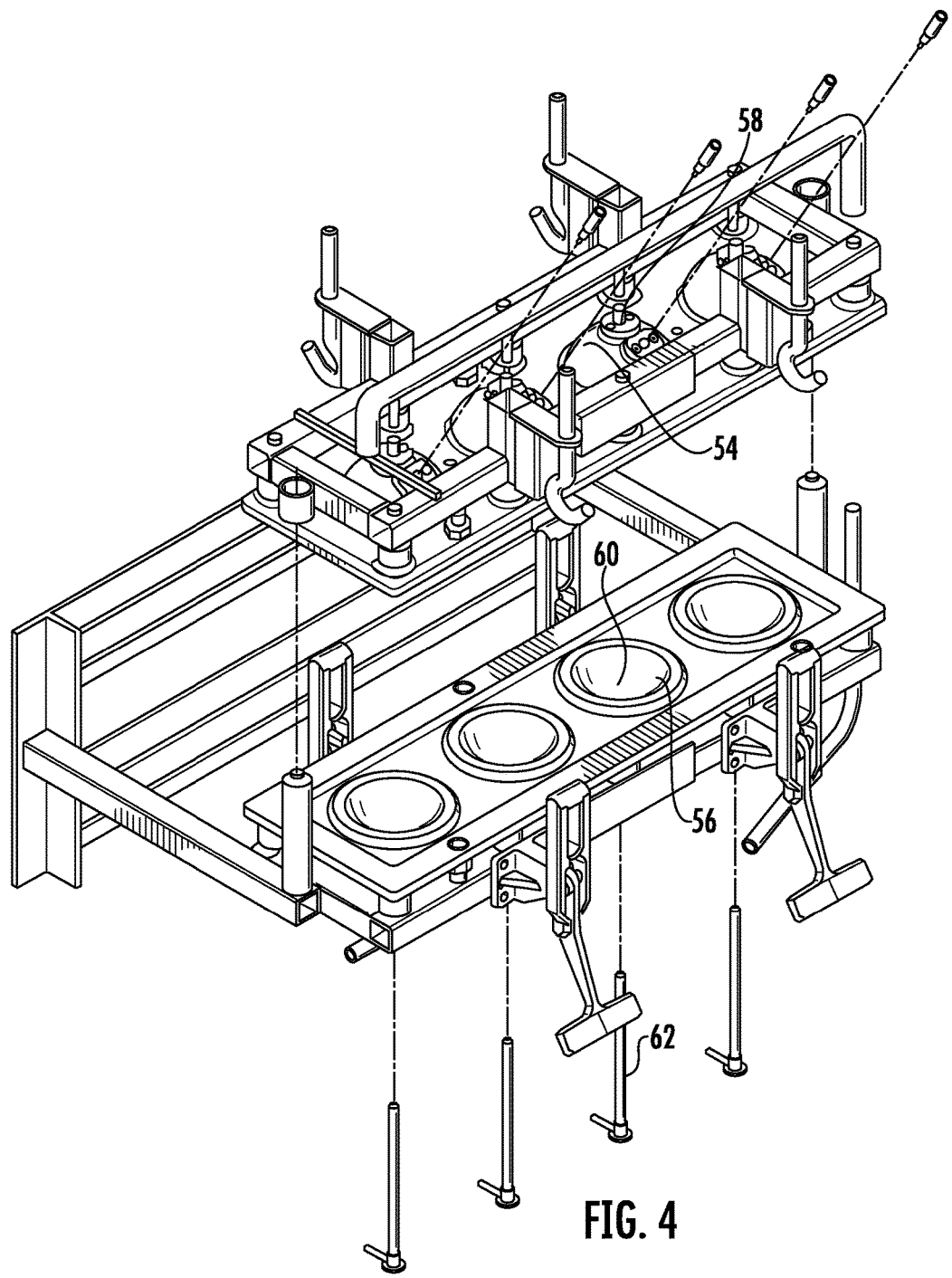
FIG. 4 illustrates a top perspective view of a rotational molding assembly used to mold the spherical container of FIG. 1.

The pain relief device is shown generally as (10) in FIG. 1. As shown, the device (10) is provided with a spherical container (12) defining an interior (14) and a side wall or tube (16) which in turn defines a channel (18) passing through the spherical container (12). The tube (16) is preferably integrally molded with the spherical container (12) in a rotational mold process but may be produced in any desired manners, including providing the tube (16) through holes (not shown) in a spherical container and adhesively securing the tube (16) to spherical container (12). In the preferred embodiment the spherical container (12) is formed from a pair of hemispherical molds (54) and (56), each having a center hole (58) and (60), through which is provided a shaft (62), which seals the center holes (58) and (60) and provides a surface on which the tube (16) is formed in the molding process. FIGS. 1 and 4 To begin the molding process, the shaft (62) is provided through the center holes (58) and (60) of the hemispherical molds (54) and (56) and the hemispherical molds (54) and (56) are sealed around a measured shot of polyethylene. The hemispherical molds (54) and (56) are heated and rotated in a manner well known in the art of rotational molding. Once the molding is complete, hemispherical molds (54) and (56) are cooled, the shaft (62) removed, the hemispherical molds (54) and (56) pulled apart, and the spherical container (12) removed. Regardless of how the spherical container (12) and tube (16) are formed, they are preferably sealed, either integrally or adhesively, into watertight engagement with one another to prevent the interior (14) from coming into fluid communication with the channel (18).

Figure 2:
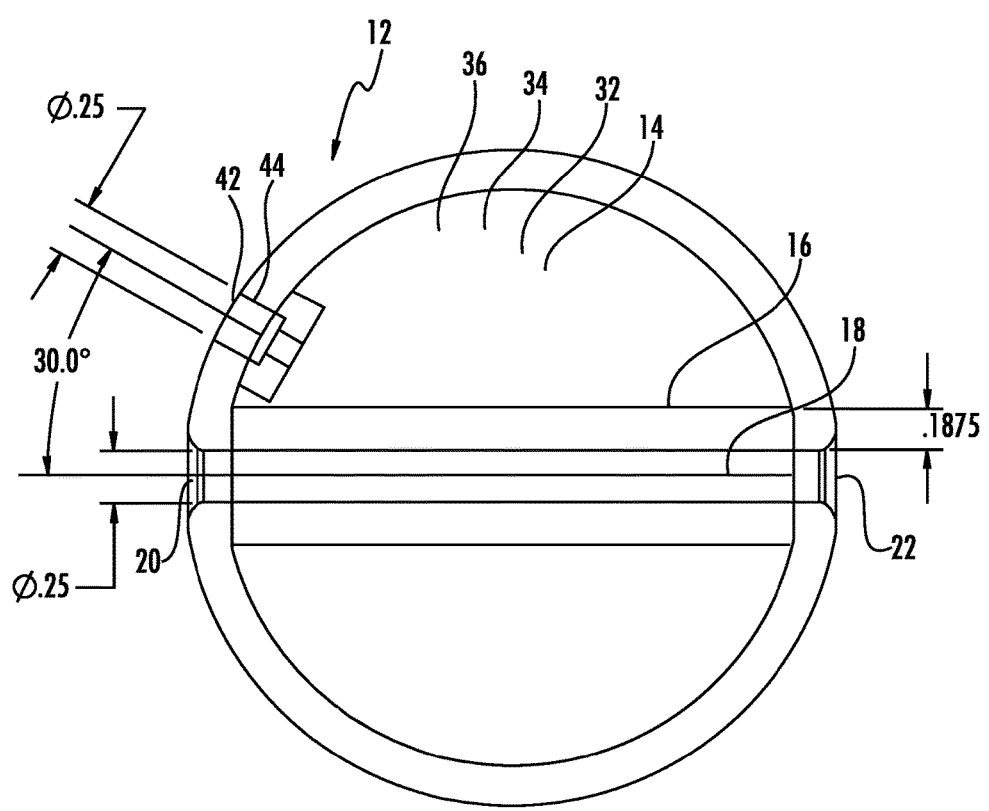
FIG. 2 illustrates a side elevation in cross-section of the spherical container of FIG. 1.

While the spherical container (12) may be constructed from any desired material, in the preferred embodiment, the spherical container (12) is constructed of a thermally conductive material such as low- or medium-density polyethylene. While the spherical container (12) is preferably rigid and not readily deformable by a user's foot (52), the spherical container (12) may be deformable as desired. Preferably, the thickness of the spherical container (12) is between 0.1 and 3 centimeters, more preferably between 0.2 and 2 centimeters, and most preferably about 0.476 centimeters. Similarly, the tube (16) is preferably 7.59 centimeters in diameter, having sidewalls of 0.476 centimeters thereby defining a channel (18) approximately 0.638 centimeters in diameter. As shown in FIG. 2, the ends of the tube (16) are provided with recesses (20) and (22) to reduce abrasion on the strap (24) provided through the channel (18). FIGS. 1-2. As shown in FIG. 1, the strap (24) is provided with a series of knots (26) defining handles (28) therebetween. While the strap (24) may be constructed of any desired material, in the preferred embodiment the strap is constructed of 550 paracord. The strap (24) may either be one long piece of paracord folded over on itself and knotted together or may be two or more separate pieces of paracord provided with knots (26) as desired to provide handles (28) in any desired location. The handle (28) may be as long or short as desired, but is preferably greater than 10 centimeters and less than 3 meters in length, more preferably greater than 20 centimeters and less than 2 meters in length, and most preferably about 2 meters in length.

As shown in FIG. 2, the spherical container (12) is provided with an opening (30) through which a mixture (32) is provided into the interior (14) of the spherical container (12). While the mixture (32) may be of any suitable combination, in the preferred embodiment, the mixture (32) is a 440:1 ratio, by weight, of a crosslinked water-absorbing mixed polymer (34), such as potassium polyacrylate and water (36). The ratio may be any desired ratio, but is preferably between 50:1 and 1000:1, more preferably between 200:1 and 600:1, and most preferably between 400:1 and 500:1. While the crosslinked water-absorbing mixed polymer (34) may be of any type known in the art, in the preferred embodiment, it is a polymer capable of absorbing a weight of water at least 50 times and more preferably 250 its weight in water. The polymer (34) may alternatively be polyacrylamide, sodium polyacrylate, or any other crosslinked water-absorbing polymer known in the art. In the preferred embodiment, a sufficient amount of polymer (34) is provided to completely absorb the water (36). The polymer (34) and water (36) may be either mixed before or after introduction into the interior (14) of the spherical container (12).

Figure 3:
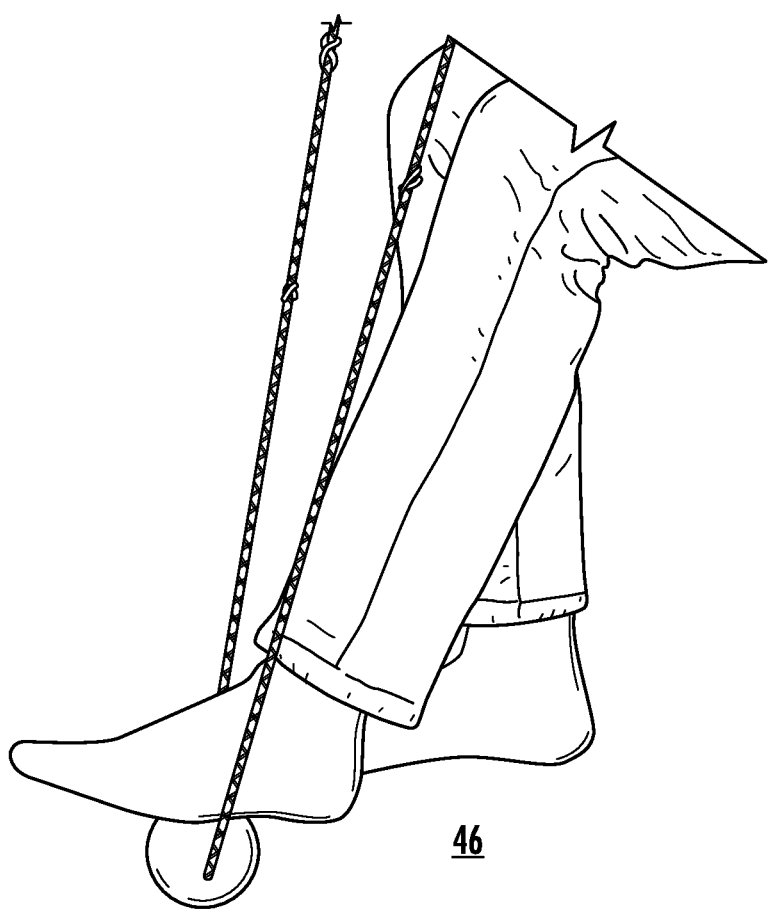
FIG. 3 illustrates a top perspective view of a user using the pain relief device in accordance with one embodiment.

Once the mixture (32) has been provided in the interior (14) of the spherical container (12) through the opening (30), a plug (42), preferably constructed of a material similar to that used to construct the spherical container (12), is secured within the open (30) by an adhesive (44) in a manner such as that known in the art to preferably provide the spherical container (12) with a smooth surface over the opening (30). Once the mixture (32) has been sealed within the interior (14) of the spherical container (12), the pain relief device (10) may be chilled to a temperature preferably below 0° Celsius, more preferably below −5° Celsius, and most preferably below −10° Celsius. Once the device (10) has been cooled, the strap (24) may be provided through the channel (18) and the spherical container (12) positioned on the floor (46) as shown in FIG. 3. A user (48) may thereafter place the bottom (50) of the user's foot (52) on the spherical container (12) and grasp the strap (24) by the handles (28) most comfortable for the user (48). The user (48) may then move the user's foot (52) back and forth across the floor (46), rolling the bottom (50) of the user's foot (52) across the spherical container (12). Alternatively, the user (48) may use the handles (28) to lift the spherical container (12) from the floor (46) to roll the spherical container (12) across the bottom (50) of the user's foot (52), instead of the user (48) having to move the user's foot (52).

In an alternative embodiment of the present invention, the user (48) may place the spherical container (12) into a hot water bath or similar apparatus (not shown) to increase the heat of the mixture (32) within the spherical container (12) to allow the user (48) to use the device (10) to apply heat to the bottom (50) of the user's foot (52) in a manner similar to that described above. Preferably, the spherical container (12) is constructed of a material which is sufficiently thermally conductive to transfer heat between the spherical container (12) and the bottom (50) of the user's foot (52).

Although the invention has been described with respect to a preferred embodiment thereof, it is to be understood that it is not to be so limited since changes and modifications can be made therein which are within the full intended scope of this invention as defined by the appended claims.

What is claimed is:

1. A heat removal relief device comprising:
a spherical container having a thermally conductive surface and defining a first hole, and a second hole;
a tube defining a channel, provided through the first hole and the second hole, and sealed into watertight engagement with the spherical container in a configuration that defines a watertight, at least partially hollow, interior within the spherical container;
a fluid mixture provided within the watertight, at least partially hollow, interior within the spherical interior;
wherein the fluid mixture comprises:
crosslinked, water-absorbing polymer;
water; and
a flexible strap provided through the channel of the tube.

2. The heat removal relief device of claim 1, wherein the crosslinked, water-absorbing polymer is capable of absorbing a weight of water at least fifty times the weight of the water-absorbing polymer.

3. The heat removal relief device of claim 2, wherein the spherical container is water impermeable.

4. The heat removal relief device of claim 1, wherein the crosslinked, water-absorbing polymer is polyacrylamide.

5. The heat removal relief device of claim 1, wherein the crosslinked, water-absorbing polymer is sodium polyacrylate.

6. The heat removal relief device of claim 1, wherein the crosslinked, water-absorbing polymer is potassium polyacrylate.

7. The heat removal relief device of claim 1, wherein the mixture further comprises a glycol.

8. The heat removal relief device of claim 1, wherein the mixture further comprises an inorganic salt.

9. The heat removal relief device of claim 1, wherein the crosslinked, water-absorbing polymer comprises discrete particles.

10. The heat removal relief device of claim 9, wherein the discrete particles are between about 50 and about 4000 microns in size.

11. The heat removal relief device of claim 1, wherein all of the water is absorbed by the crosslinked, water-absorbing polymer.

12. The heat removal relief device of claim 1, wherein the spherical container is rigid.

13. The heat removal relief device of claim 1, wherein the spherical container is constructed of polyethylene.

14. The heat removal relief device of claim 1, wherein the spherical container defines an opening in fluid communication with the interior of the spherical container and an exterior of the spherical container.

15. The heat removal relief device of claim 14, further comprising a plug provided within the opening.

16. The heat removal relief device of claim 1, wherein the spherical container defines a first recessed opening to the channel and a second recessed opening to the channel.

17. The heat removal relief device of claim 1, wherein the mixture is at a temperature below 0° Celsius.

* * * * *